United States Patent
Harding et al.

(10) Patent No.: US 6,830,934 B1
(45) Date of Patent: Dec. 14, 2004

(54) MICRODROPLET DISPENSING FOR A MEDICAL DIAGNOSTIC DEVICE

(75) Inventors: Ian A. Harding, San Mateo, CA (US); Robert Justice Shartle, Livermore, CA (US); Glenn Renowitzky, San Lorenzo, CA (US); Lewis Leung, Fremont, CA (US)

(73) Assignee: LifeScan, Inc., Milpitas, CA (US)

( * ) Notice: Subject to any disclaimer, the term of this patent is extended or adjusted under 35 U.S.C. 154(b) by 0 days.

(21) Appl. No.: 09/454,196

(22) Filed: Dec. 3, 1999

Related U.S. Application Data

(63) Continuation-in-part of application No. 09/333,765, filed on Jun. 15, 1999, now Pat. No. 6,521,182.

(51) Int. Cl.[7] ............................. B05D 3/00; G01N 21/75
(52) U.S. Cl. ........................ 436/166; 436/169; 422/58; 347/98; 427/2.11
(58) Field of Search .............................. 422/56, 58, 61; 436/164, 169, 166; 347/98; 427/2.11; 530/351; 435/174

(56) References Cited

U.S. PATENT DOCUMENTS

| | | | |
|---|---|---|---|
| 3,620,676 A | 11/1971 | Davis ........................... 23/253 |
| 3,640,267 A | 2/1972 | Hurtig et al. ................... 128/2 |
| 4,088,448 A | 5/1978 | Lilja et al. ..................... 23/259 |
| 4,756,884 A | 7/1988 | Hillman et al. |
| 4,849,340 A | 7/1989 | Oberhardt |
| 4,877,745 A | * 10/1989 | Hayes et al. ................. 436/166 |
| 5,068,181 A | 11/1991 | Driscoll |
| 5,108,926 A | 4/1992 | Klebe .......................... 435/284 |
| 5,208,163 A | 5/1993 | Charlton et al. |
| 5,378,638 A | 1/1995 | Deeg et al. .................. 436/518 |
| 5,508,521 A | 4/1996 | Kraft et al. |
| 5,591,403 A | 1/1997 | Gavin et al. |
| 5,610,287 A | * 3/1997 | Nikiforov et al. .......... 435/180 |
| 5,628,961 A | 5/1997 | Davis et al. |
| 5,677,195 A | 10/1997 | Winkler et al. |
| 6,066,448 A | * 5/2000 | Wohlstadter et al. ....... 204/400 |
| 6,066,504 A | * 5/2000 | Jina ............................. 436/69 |
| 6,103,196 A | 8/2000 | Yassinzadeh et al. |

FOREIGN PATENT DOCUMENTS

| | | |
|---|---|---|
| EP | 0 974 840 A | 1/2000 |
| GB | 1526708 | 9/1978 |
| WO | WO94/02850 | 2/1994 |

OTHER PUBLICATIONS

Stimpson, Donald, et al. "Parallel production of oligonucleotide arrays using membranes and reagent jet printing", Biotechniques, vol. 25, No. 5, Nov. 1998, pp. 886–890.

* cited by examiner

*Primary Examiner*—Lyle A. Alexander
(74) *Attorney, Agent, or Firm*—Carol M. LaSalle; Bozicevic, Field & Francis LLP

(57) ABSTRACT

A medical diagnostic device has a non-absorbent substrate that has a hydrophilic target area on which a reagent is deposited by non-impact printing of microdroplets. During deposition, the device is moved relative to the stream of microdroplets to form a substantially uniform reagent layer on the substrate. The device is particularly well adapted for measuring blood coagulation times. In a preferred embodiment, coagulation times are determined by monitoring the optical transmission of light through the target area as an applied blood sample interacts with the reagent.

11 Claims, 9 Drawing Sheets

MICRODROPLET DISPENSING FOR A MEDICAL DIAGNOSTIC DEVICE

CROSS-REFERENCE TO PRIOR APPLICATION

This application is a continuation-in-part of Application Ser. No. 09/333,765, filed Jun. 15, 1999 now U.S. Pat. No. 6,521,182.

BACKGROUND OF THE INVENTION

1. Field of the Invention

This invention relates to a medical diagnostic device that is prepared by nonimpact printing; more particularly, by nonimpact printing of a reagent onto a hydrophilic surface of the device.

2. Description of the Related Art

A variety of medical diagnostic procedures involve tests on biological fluids, such as blood, urine, or saliva, and are based on a change in a physical characteristic of such a fluid or an element of the fluid, such as blood serum. The characteristic can be an electrical, magnetic, fluidic, or optical property. When an optical property is monitored, these procedures may make use of a transparent or translucent device to contain the biological fluid and a reagent. A change in light absorption of the fluid can be related to an analyte concentration in, or property of, the fluid. Typically, a light source is located adjacent to one surface of the device and a detector is adjacent to the opposite surface. The detector measures light transmitted through a fluid sample. Alternatively, the light source and detector can be on the same side of the device, in which case the detector measures light scattered and/or reflected by the sample. Finally, a reflector may be located at or adjacent to the opposite surface. A device of this latter type, in which light is first transmitted through the sample area, then reflected through a second time, is called a "transflectance" device. References to "light" throughout this specification and the appended claims should be understood to include the infrared and ultraviolet spectra, as well as the visible. References to "absorption" are meant to refer to the reduction in intensity as a light beam passes through a medium; thus, it encompasses both "true" absorption and scattering.

An example of a transparent test device is described in Wells et al. WO94/02850, published on Feb. 3, 1994. Their device comprises a sealed housing, which is transparent or translucent, impervious, and rigid or semi-rigid. An assay material is contained within the housing, together with one or more assay reagents at predetermined sites. The housing is opened and the sample introduced just before conducting the assay. The combination of assay reagents and analyte in the sample results in a change in optical properties, such as color, of selected reagents at the end of the assay. The results can be read visually or with an optical instrument.

U.S. Pat. No. 3,620,676, issued on Nov. 16, 1971 to Davis, discloses a colorimetric indicator for liquids. The indicator includes a "half-bulb cavity", which is compressible. The bulb is compressed and released to form a suction that draws fluid from a source, through a half-tubular cavity that has an indicator imprinted on its wall. The only controls on fluid flow into the indicator are how much the bulb is compressed and how long the indicator inlet is immersed in the source, while the bulb is released.

U.S. Pat. No. 3,640,267, issued on Feb. 8, 1972 to Hurtig et al., discloses a container for collecting samples of body fluid that includes a chamber that has resilient, collapsible walls. The walls are squeezed before the container inlet is placed into the fluid being collected. When released, the walls are restored to their uncollapsed condition, drawing fluid into and through the inlet. As with the Davis device, discussed above, control of fluid flow into the indicator is very limited.

U.S. Pat. No. 4,088,448, issued on May 9, 1978 to Lilja et al., discloses a cuvette, which permits optical analysis of a sample mixed with a reagent. The reagent is coated on the walls of a cavity, which is then filled with a liquid sample. The sample mixes with the reagent to cause an optically-detectable change.

The test devices described above and in the cited references typically comprise a dry strip having a reagent coated on one or more predetermined positions. Applying these reagents to their intended positions on large numbers of these devices can, in principle, be accomplished by standard printing processes; however, nonimpact printing provides some distinct advantages. For example, nonimpact printers can be smaller, lighter, and less expensive, since they don't have to endure the repeated impact of print head on substrate. They also permit the use of transparent substrates, as required for optical devices that involve changes in light transmission. Information on the varieties of nonimpact printing appears in J. L. Johnson, Principles of Nonimpact Printing, 3d ed., Palatino Press, Irvine, Calif. 1998. (See, also, "No-splatter spray makes better wafers," H. L. Berger, Machine Design, Feb. 5, 1998, pp. 52–55). Among the varieties of nonimpact printing, ink-jet printing has been identified as suitable for use in connection with reagent fluids.

British Patent Specification, 1,526,708, published on Sep. 27, 1978, discloses a reagent test device that comprises a carrier on which are printed two different substances, separated by a "predetermined interspace." Ink-jet printing is one of the printing techniques disclosed.

U.S. Pat. No. 4,877,745, issued on Oct. 31, 1989, to Hayes et al., discloses a system for printing reagents onto a printing medium by propelling droplets from a jetting tube and repeating the process until a desired configuration of the reagent is printed on the medium. A piezo-electric print head was used.

U.S. Pat. No. 5,108,926, issued on Apr. 28, 1992, to Klebe; discloses an apparatus for precisely locating cells on a substrate by using an ink-jet printer either to deposit the cells directly onto the substrate or to deposit cell adhesion materials. The ink-jet printer used was a Hewlett-Packard Thinkjet™ printer, which is a thermal ink-jet printer (see Hewlett-Packard Journal, May, 1985).

U.S. Pat. No. 5,378,638, issued on Jan. 3, 1995, to Deeg et al., discloses an analysis element for the determination of an analyte in a liquid sample. The element is fabricated by ink-jet printing of reagents in a series of "compartments," using a thermal ink-jet print head.

Each of the references cited above are concerned, explicitly or implicitly, with image spreading on the print medium, because the sharpness of an image is degraded to the extent that the liquid "ink" spreads across the surface before drying. For diagnostic applications, sharp "images" are typically required, because different reagents are positioned close together on a surface of a device but must not come into contact (e.g., to react) until the device is wetted by an applied sample.

SUMMARY OF THE INVENTION

The present invention provides a method for preparing a medical diagnostic reagent device, comprising the steps of a) providing a non-absorbent substrate, having on its surface at least one hydrophilic target area, b) providing from a nonimpact print head onto a point within the target area a pulsed stream of microdroplets of a diagnostic reagent liquid, c) moving the stream relative to the substrate, and d) repeating steps b) and c) at least enough times to provide a substantially uniform layer of the liquid over the target area.

A diagnostic reagent device of the present invention measures analyte concentration or characteristic of a biological fluid and comprises a) a sample application area for accepting a sample of the biological fluid for analysis and b) a predetermined hydrophilic reagent area, onto which has been applied, by nonimpact printing, a diagnostic reagent liquid that interacts with the sample to cause in the sample a physically-measurable change that can be related to the analyte concentration or characteristic of the fluid.

The sample application and reagent areas may coincide or, alternatively, be spaced apart, with an intermediate path to convey the sample. The measurement is generally, but not necessarily, made when the sample is on the reagent area, and in the description below, the measurement of interest is made when the sample is in the reagent area.

The method is particularly well adapted for preparing a device for measuring prothrombin time (PT time), with the target area being coated with a reagent composition that catalyzes the blood clotting cascade. Similarly, the diagnostic reagent strip of the invention is particularly well adapted for measuring the PT time of a whole blood sample.

As used in this specification and the appended claims, the term "microdrdplet" refers to droplets having a volume in the range from about 1 picoliter to 1 microliter.

It is surprising that the hydrophilicity of the target area provides superior results, since the hydrophilic surface would be expected to spread the reagent that is deposited, which had been thought to be undesirable.

DETAILED DESCRIPTION OF THE INVENTION

Figure 1:
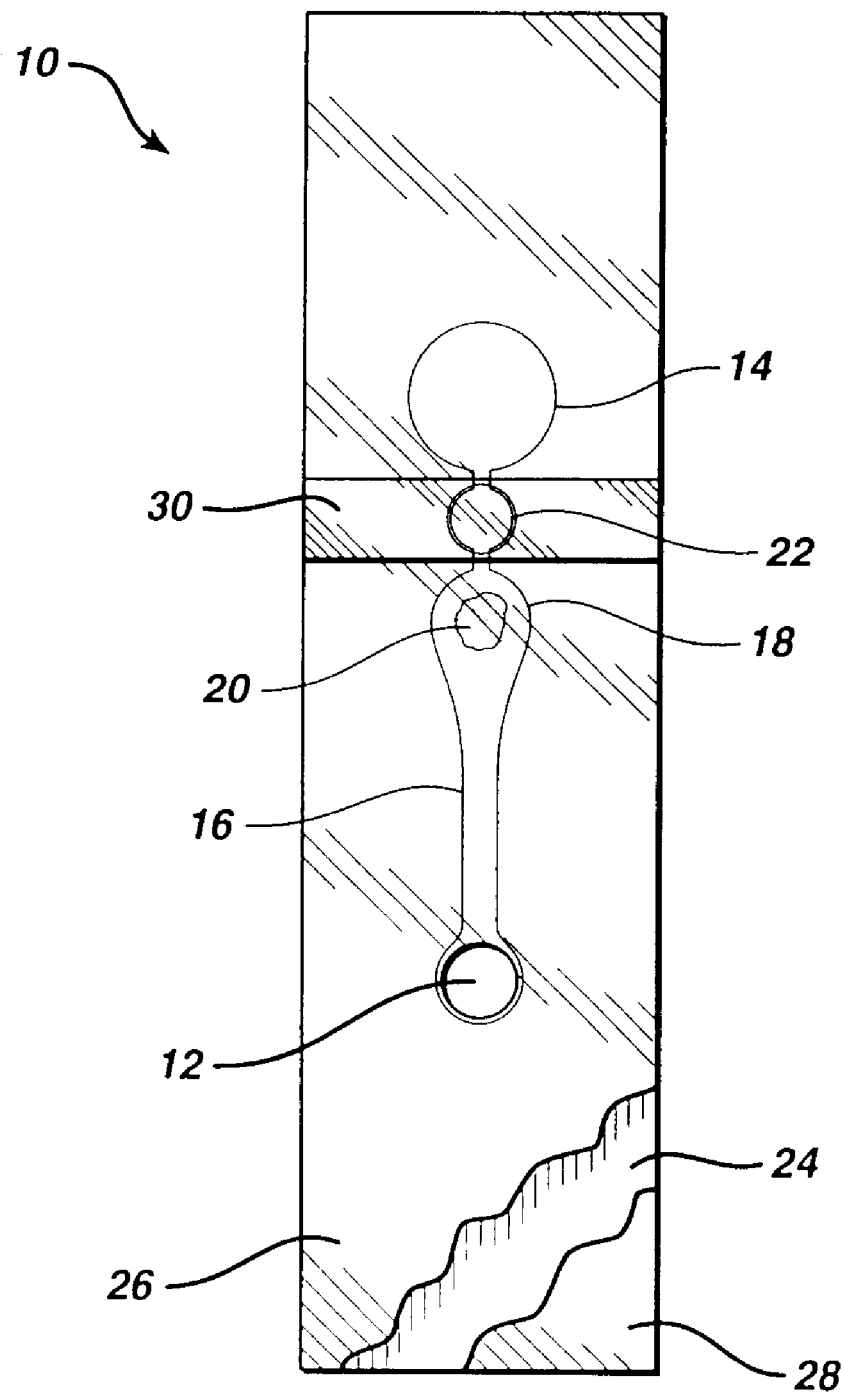
FIG. 1 is a plan view of a device of the present invention.

The medical diagnostic reagent device of this invention is prepared by depositing a reagent upon a hydrophilic "reagent area" of a non-absorbent substrate by a nonimpact printing process. The device is of the type that relates a physical parameter of a biological fluid, or an element of the fluid, to an analyte concentration in the fluid or to a property of the fluid. Although a variety of physical parameters—e.g., electrical, magnetic, fluidic, or optical—can form the basis for the measurement, a change in optical parameters is a preferred basis, and the details that follow refer to an optical device. A preferred embodiment of the device includes a planar substrate, such as a thermoplastic sheet. The substrate has on its surface a sample application area and the reagent area, in which the sample undergoes a change in an optical parameter, such as light scattering. The substrate, or "bottom layer," forms with "intermediate" and "top" layers a bladder, to create a suction force to draw the sample into the device, and a stop junction, to precisely stop flow after filling the reagent area.

Preferably, the device is substantially transparent over the reagent area, so that the area can be illuminated by a light source on one side and the transmitted light measured on the opposite side. The nonimpact-printed reagent causes the sample to undergo a change, and the change in transmitted light is a measure of the analyte or fluid property of interest. Alternatively, light that is scattered from a fluid sample or light that passes through the sample and is reflected back through a second time (by a reflector on that opposite side) can be detected by a detector on the same side as the light source.

This type of device is suitable for a variety of analytical tests of biological fluids, such as determining biochemical or hematological characteristics, or measuring the concentration in such fluids of proteins, hormones, carbohydrates, lipids, drugs, toxins, gases, electrolytes, etc. The procedures for performing these tests have been described in the literature. Among the tests, and where they are described, are the following:

(1) Chromogenic Factor XIIa Assay (and other clotting factors as well): Rand, M. D. et al., Blood, 88, 3432 (1996).

(2) Factor X Assay: Bick, R. L. Disorders of Thrombosis and Hemostasis: Clinical and Laboratory Practice. Chicago, ASCP Press, 1992.

(3) DRVVT (Dilute Russells Viper Venom Test): Exner, T. et al., Blood Coag. Fibrinol., 1, 259 (1990).

(4) Immunonephelometric and Immunoturbidimetric Assays for Proteins: Whicher, J. T., CRC Crit. Rev. Clin LabSci. 18:213 (1983).

(5) TPA Assay: Mann, K. G., et al., Blood, 76, 755, (1990).; and Hartshorn, J. N. et al., Blood, 78, 833 (1991).

(6) APTT (Activated Partial Thromboplastin Time Assay): Proctor, R. R. and Rapaport, S. I. Amer. J. Clin. Path, 36, 212 (1961); Brandt, J. T. and Triplett, D. A. Amer. J. Clin. Path., 76, 530 (1981); and Kelsey, P. R. Thromb. Haemost. 52, 172 (1984).

(7) HbA1c Assay (Glycosylated Hemoglobin Assay): Nicol, D. J. et al., Clin. Chem. 29, 1694 (1983).

(8) Total Hemoglobin: Schneck et al., Clinical Chem., 32/33, 526 (1986); and U.S. Pat. No. 4,088,448.

(9) Factor Xa: Vinazzer, H., Proc. Symp. Dtsch. Ges. Klin. Chem., 203 (1977), ed. By Witt, I

(10) Colorimetric Assay for Nitric Oxide: Schmidt, H. H., et al., Biochemica, 2, 22 (1995).

The present device is particularly well suited for measuring blood-clotting time—"prothrombin time" or "PT time"—and details regarding such a device appear below. The modifications needed to adapt the device for applications such as those listed above require no more than routine experimentation.

Figure 2:
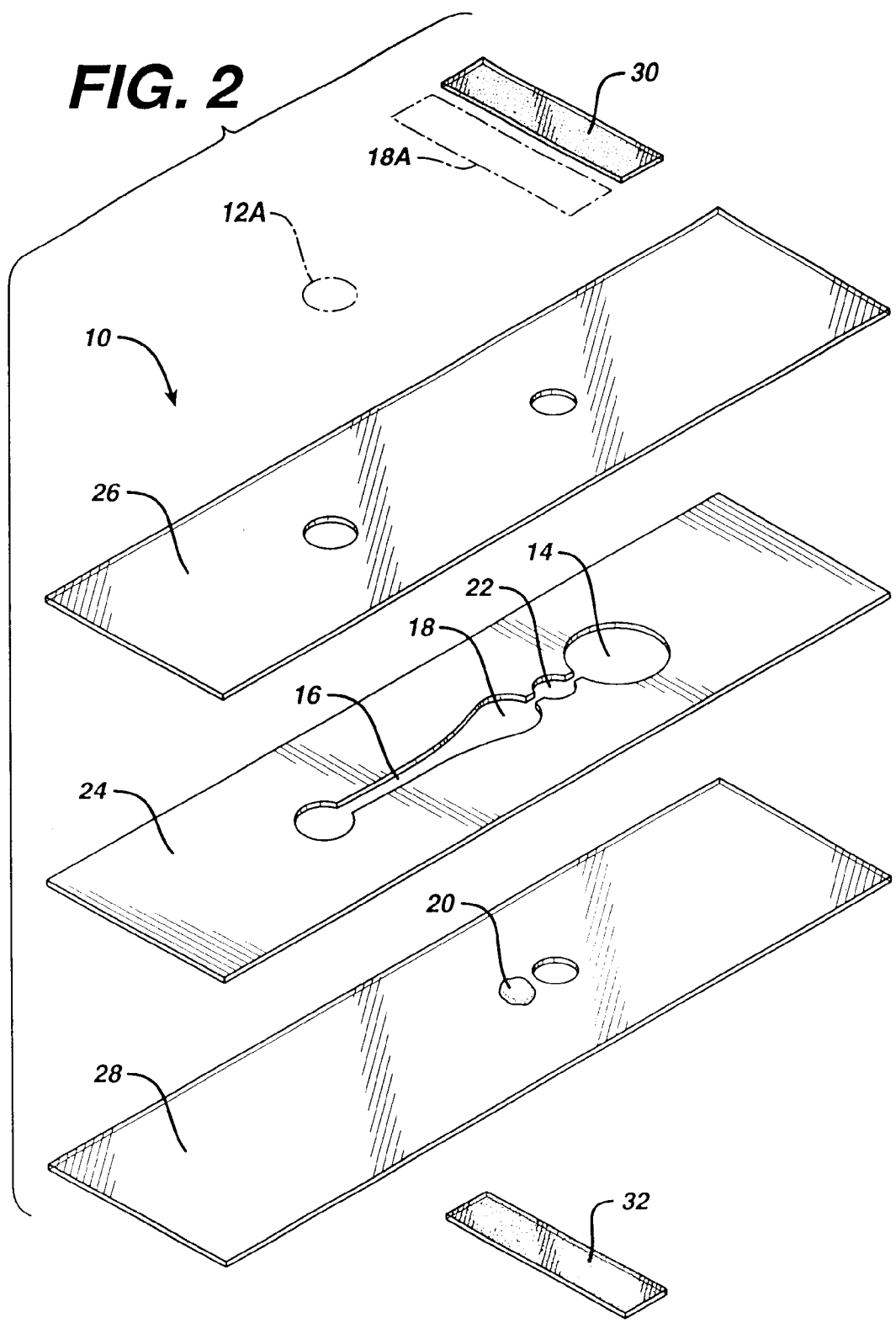
FIG. 2 is an exploded view of the device of FIG. 1.

FIG. 1 is a plan view of a device 10 of the present invention. FIG. 2 is an exploded view and FIG. 3 a perspective view of the device. Sample is applied to sample port 12 after bladder 14 has been compressed. Clearly, the region of layer 26 and/or layer 28 that adjoins the cutout for bladder 14 must be resilient, to permit bladder 14 to be compressed. Polyester of about 0.1 mm thickness has suitable resilience and springiness. Preferably, top layer 26 has a thickness of about 0.125 mm, bottom layer 28 about 0.100 mm. When the bladder is released, suction draws sample through channel 16 to reagent area 18, which contains a nonimpact-printed reagent 20. In order to ensure that reagent area 18 can be filled with sample, the volume of bladder 14 is preferably at least about equal to the combined volume of channel 16 and reagent area 18. If reagent area 18 is to be illuminated from below, layer 28 must be transparent where it adjoins reagent area 18. For a PT test, reagent 20 contains thromboplastin that is free of bulking reagents normally found in lyophilized reagents.

Figure 3:
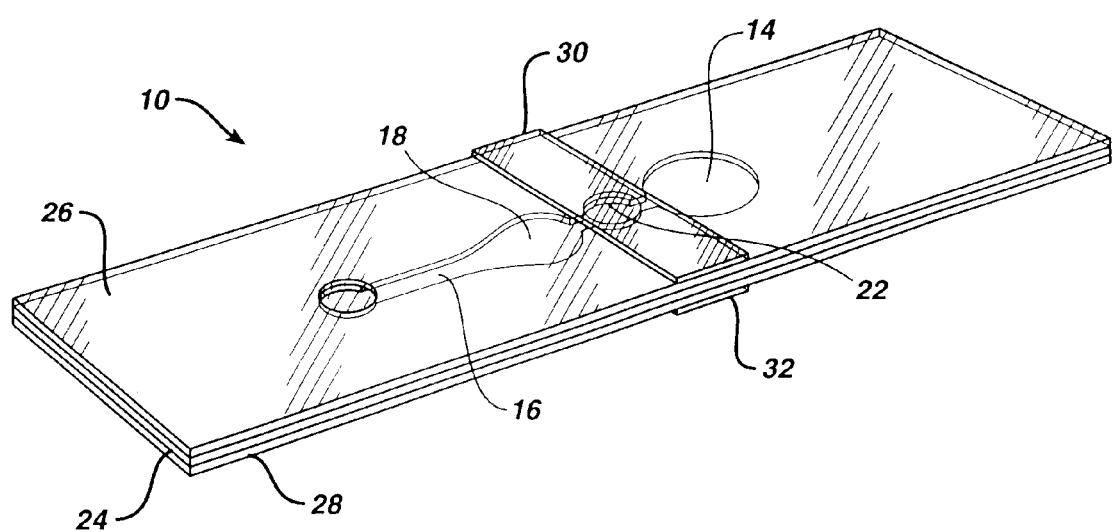
FIG. 3 is a perspective view of the device of FIG. 1.

As shown in FIGS. 1, 2, and 3, stop junction 22 adjoins bladder 14 and reagent area 18; however, a continuation of channel 16 may be on either or both sides of stop junction 22, separating the stop junction from reagent area 18 and/or bladder 14. When the sample reaches stop junction 22, sample flow stops. For PT measurements, it is important to stop the flow of sample as it reaches that point to permit reproducible "rouleaux formation" —the stacking of red blood cells—which is an important step in monitoring blood clotting using the present invention. The principle of operation of stop junctions is described in U.S. Pat. No. 5,230,866, incorporated herein by reference.

As shown in FIG. 2, all the above elements are formed by cutouts in intermediate layer 24, sandwiched between top layer 26 and bottom layer 28. Preferably, layer 24 is double-sided adhesive tape. Stop junction 22 is formed by an additional cutout in layer 26 and/or 28, aligned with the cutout in layer 24 and sealed with sealing layer 30 and/or 32. Preferably, as shown, the stop junction comprises cutouts in both layers 26 and 28, with sealing layers 30 and 32. Each cutout for stop junction 22 is at least as wide as channel 16. Also shown in FIG. 2 is an optional filter 12A to cover sample port 12. The filter may separate out red blood cells from a whole blood sample and/or may contain a reagent to interact with the blood to provide additional information. A suitable filter comprises an anisotropic membrane, preferably a polysulfone membrane of the type available from Spectral Diagnostics, Inc., Toronto, Canada. Optional reflector 18A maybe on, or adjacent to, a surface of layer 26 and positioned over reagent area 18. If the reflector is present, the device becomes a transflectance device.

Figure 4:
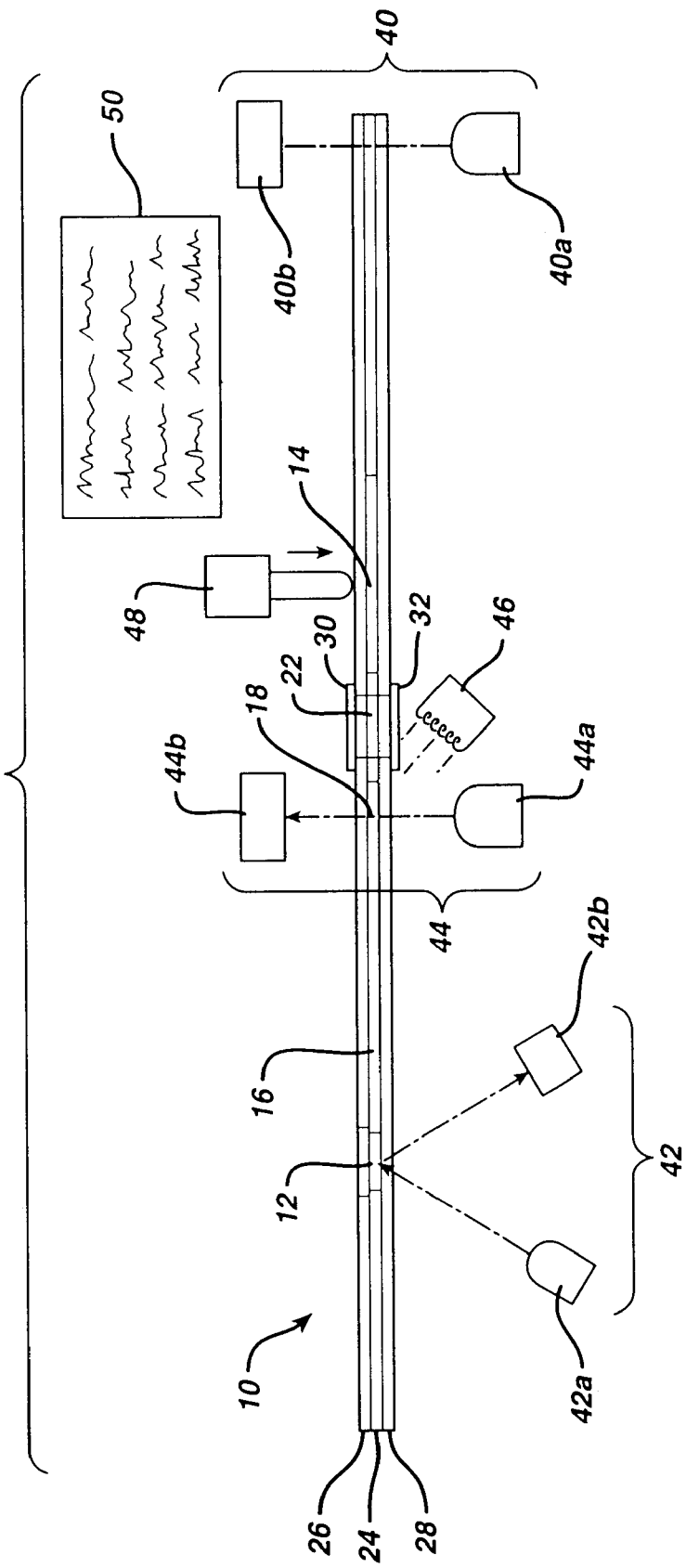
FIG. 4 is a schematic of a meter for use with a device of this invention.

The method of using the strip of FIGS. 1, 2, and 3 can be understood with reference to a schematic of the elements of a meter shown in FIG. 4, which contemplates an automated meter. Alternatively, manual operation is also possible. (In that case, bladder 14 is manually depressed before sample is applied to sample port 12, then released.)

The first step the user performs is to turn on the meter, thereby energizing strip detector 40, sample detector 42, measurement system 44, and optional heater 46. The second step is to insert the strip. Preferably, the strip is not transparent over at least a part of its area, so that an inserted strip will block the illumination by LED 40a of detector 40b. (More preferably, the intermediate layer is formed of a nontransparent material, so that background light does not enter measurement system 44.) Detector 40b thereby senses that a strip has been inserted and triggers bladder actuator 48 to compress bladder 14. A meter display 50 then directs the user to apply a sample to sample port 12 as the third and last step the user must perform to initiate the measurement sequence.

The empty sample port is reflective. When a sample is introduced into the sample port, it absorbs light from LED 42a and thereby reduces the light that is reflected to detector 42b. That reduction in light, in turn, signals actuator 48 to release bladder 14. The resultant suction in channel 16 draws sample through reagent area 18 to stop junction 22. Light from LED 44a passes through reagent area 18, and detector 44b monitors the light transmitted through the sample as it is clotting. When there are multiple reagent areas, measurement system 44 includes an LED/detector pair (like 44a and 44b) for each reagent area. Analysis of the transmitted light as a function of time (as described below) permits a calculation of the PT time, which is displayed on the meter display 50. Preferably, sample temperature is maintained at about 37° C. by heater 46.

Figure 5:
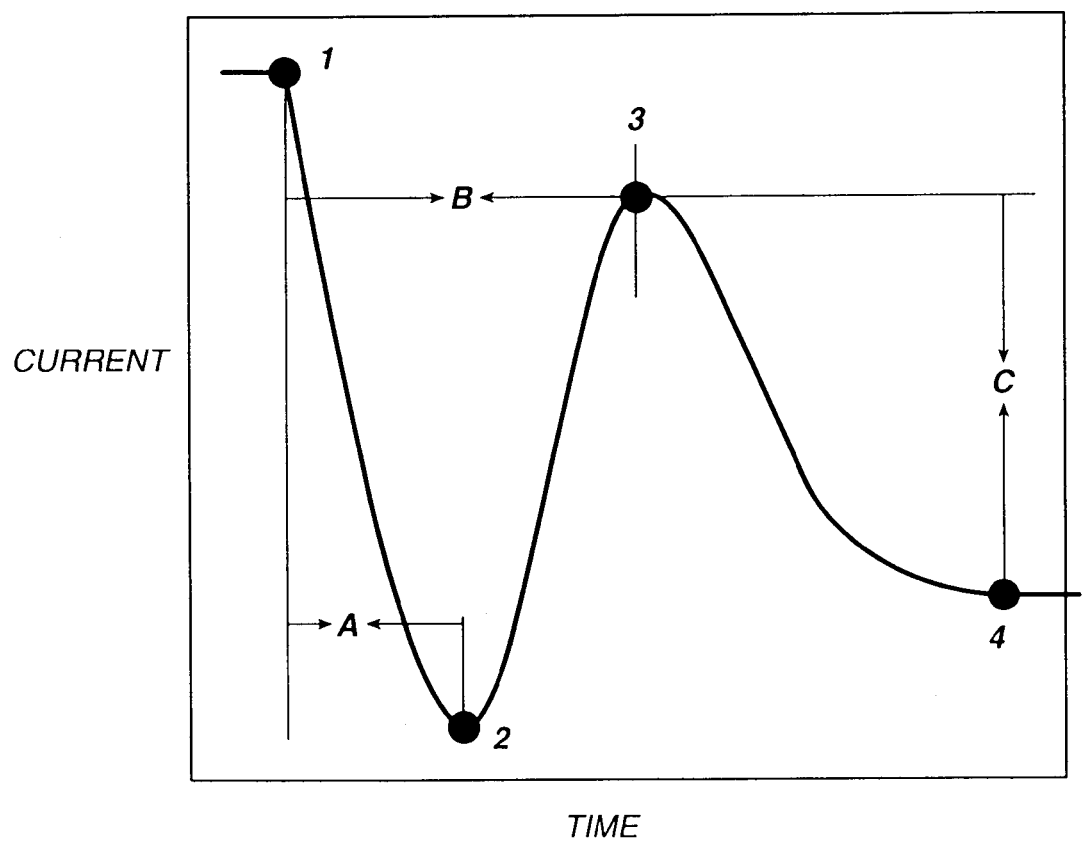
FIG. 5 is a graph of data that is used to determine PT time.

FIG. 5 depicts a typical "clot signature" curve in which the current from detector 44b is plotted as a function of time. Blood is first detected in the reagent area by 44b at time 1. In the time interval A, between points 1 and 2, the blood fills the reagent area. The reduction in current during that time interval is due to light scattered by red cells and is thus an approximate measure of the hematocrit. At point 2, sample has filled the reagent area and is at rest, its movement having been stopped by the stop junction. The red cells begin to stack up like coins (rouleaux formation). The rouleaux effect allows increasing light transmission through the sample (and less scattering) in the time interval between points 2 and 3. At point 3, clot formation ends rouleaux formation and transmission through the sample reaches a maximum. The PT time can be calculated from the interval B between points 1 and 3 or between 2 and 3. Thereafter, blood changes state from liquid to a semi-solid gel, with a corresponding reduction in light transmission. The reduction in current C between the maximum 3 and endpoint 4 correlates with fibrinogen in the sample.

Figure 6:
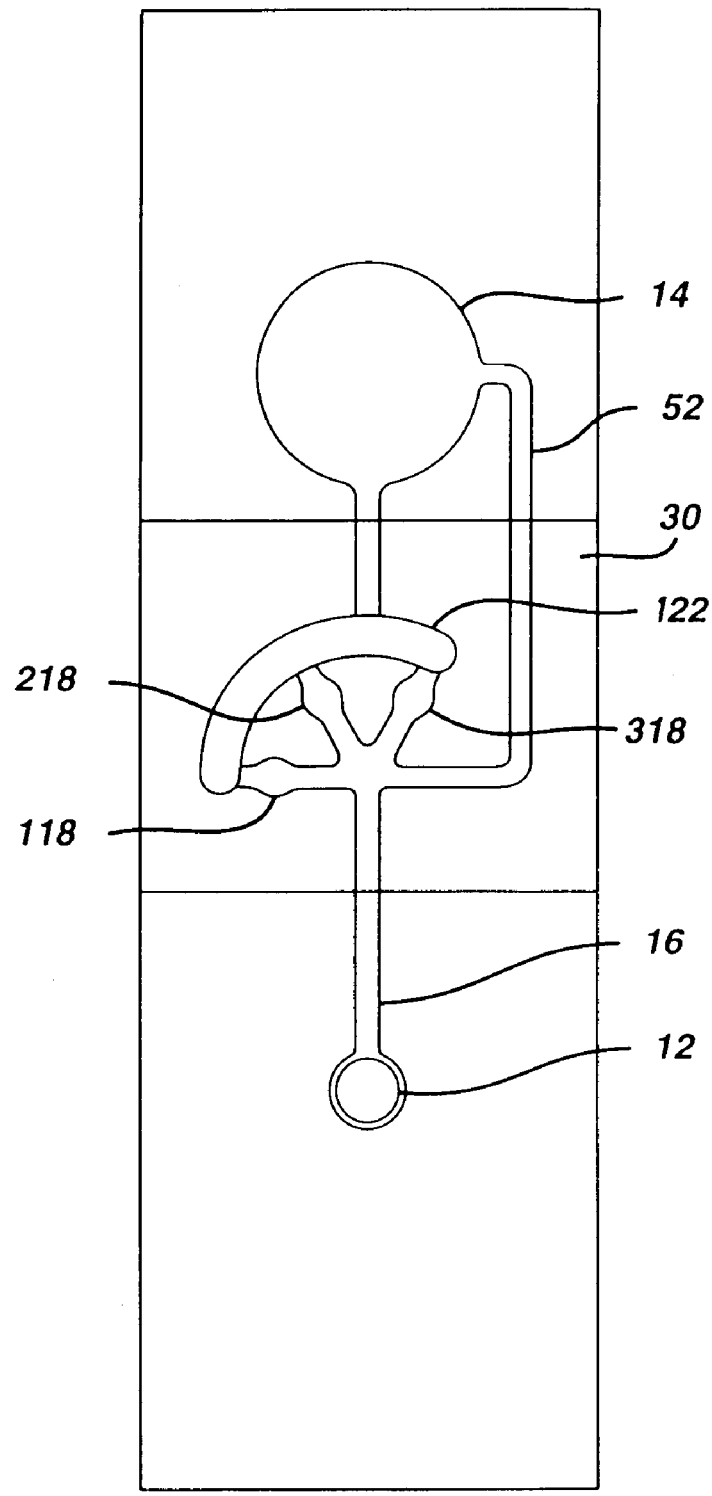
FIG. 6 is a plan view of an alternative embodiment of a device of this invention.

FIG. 6 depicts a preferred embodiment of the present device. It is a multi-channel device that includes a bypass channel 52. Bypass channel 52 provides a path for sample to travel after sample has been drawn into reagent areas 118, 218, and 318. Sample is drawn into the bypass channel by the reduced pressure on the bladder side of stop junction 122. Sample flow stops when the ambient pressure is equalized on both sides of the stop junction. Reagent area 118 contains thromboplastin. Preferably, reagent areas 218 and 318 contain controls, more preferably, the controls described below. Area 218 contains thromboplastin, bovine eluate, and recombinant Factor VIIa. The composition is selected to normalize the clotting time of a blood sample by counteracting the effect of an anticoagulant, such as warfarin. Reagent area 318 contains thromboplastin and bovine eluate alone, to partially overcome the effect of an anticoagulant. Thus, three measurements are made on the strip. PT time of the sample, the measurement of primary interest, is measured on area 118. However, that measurement is validated only when measurements on areas 218 and 318 yield results within a predetermined range. If either or both of these control measurements are outside the range, then a retest is indicated. Extended stop junction 122 stops flow in all three reagent areas.

The device pictured in FIGS. 1 and 2 and described above is preferably formed by laminating thermoplastic sheets 26 and 28 to a thermoplastic intermediate layer 24 that has adhesive on both of its surfaces. The cutouts that form the elements shown in FIG. 1 may be formed, for example, by laser—or die-cutting of layers 24, 26, and 28.

The reagent area 18 on bottom layer 28 is defined by the cutout in intermediate layer 24. Preferably, the bottom surface of top layer 26, facing bottom layer 28, is hydrophobic, at least in the region of channel 16 and reagent area 18. The surface of reagent area 18 is hydrophilic. Preferably, the surface of sample port 12 is hydrophilic as well, to facilitate filling of the device; i.e., moving the sample from port 12 to reagent area 18. A convenient way to have hydrophilic sample and reagent areas is to have the entire surface of bottom layer 28 be hydrophilic. Commercially available thermoplastic films having suitably hydrophilic surfaces include 3M 9962 Antifog Film ("Antifog"), available from Medical Specialties, 3M Health Care, St. Paul, Minn; FMC GelBondFilm, available from Bio Whittaker Molecular Applications, Rockland, Me.; polyethylene terephthalate (PET) film, whose surface has been flame-corona—or plasma-treated; ionomer film; and other conventional thermoplastic films having hydrophilic surfaces or coatings. The Antifog is PET film coated with a 3M-proprietary coating and is the preferred substrate material.

In determining the suitability of a substrate for the present device and method, the surface hydrophilicity can be determined in several different ways.

Contact angle is nominally the angle between the edge of a drop of fluid (usually purified water) that sits atop a wettable surface and the surface itself. The method for measuring the contact angle has been standardized, and can be carried out using manual or automated equipment. (ASTM Test Method D5946-96, Standard Test Method for Corona-Tested Polymer Films Using Water Contact Angle Measurements.) The data can generally by considered accurate and reproducible when the measured angle is greater than 25°, and films are considered quite wettable if the contact angle is about 60° or less. The angles measured for Antifog were about 25°.

Wetting tension is measured by spreading solutions of known surface tension onto a surface to be tested and observing if the solutions "bead up." (ASTM Test Method D2578-94, Standard Test Method for Wetting Tension of Polyethylene and Polypropylene Films). Beading up indicates that internal liquid attractive forces overcome adsorptive attraction of the surface. The solutions are calibrated in units of dynes/cm, and are referred to as dyne solutions. They are commercially available in the range of 30 to 60 dynes/cm. A surface is tested starting with the lowest value solution and progressing to the highest. A surface is assigned the dyne/cm value corresponding to that solution that remains spread out for approximately two seconds. Since Antifog wetted out all the solutions, it has been characterized as having a surface wetting tension greater than 60 dynes/cm.

3M's Medical Specialties Department has developed a wetting test to characterize water-wetting of film. (3M SMD #6122, Wetting Test, Dec. 4, 1998—available from 3M Center, St. Paul, Minn. 55144-1000.) The test involves careful placement of an aqueous dye solution onto a surface, drying it, and measuring the diameter of the dried spots. The data collected were generally in the 35 to 40 point range, which indicates a very wettable surface.

Based on the measurements described above, we conclude that the Antifog surface is extremely hydrophilic. When a surface is adequately hydrophilic, then reagent droplets spread over the surface and, providing sufficient droplets are deposited, form a substantially uniform layer of the reagent over the desired area. As used in this specification and the appended claims, the term "substantially uniform" should not be construed as necessarily suggesting that the surface coating thickness is the same over the entire target area, nor even that the entire surface is coated.

Figure 7:
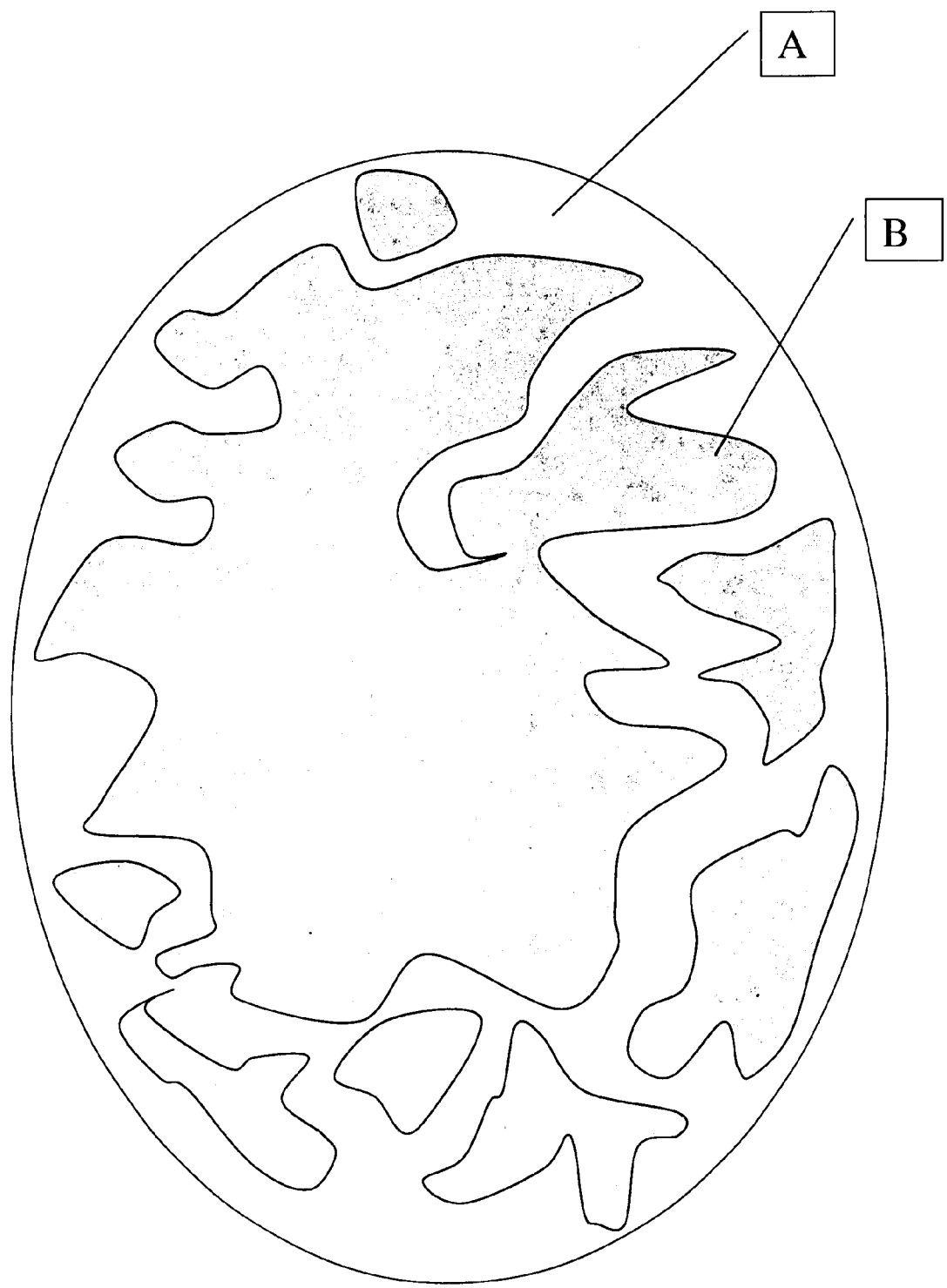
FIGS. 7 (A–B) is a plan view of a coating prepared by the method of the present invention.

FIG. 7 depicts a plan view of part of a typical coated target area. Note that part of the surface (A) remains uncoated, although most of the surface (B) is coated. Preferably, at least about 80% of the target area is coated. Preferably, thickness variations in the coated areas (B) are minimized; e.g., thickest region less than three times the average thickness of the coated area. Average coating thickness in coated areas is generally about 0.1 micrometer—about 1 micrometer, depending on the nature of the reagent and the particular application.

Figure 8:
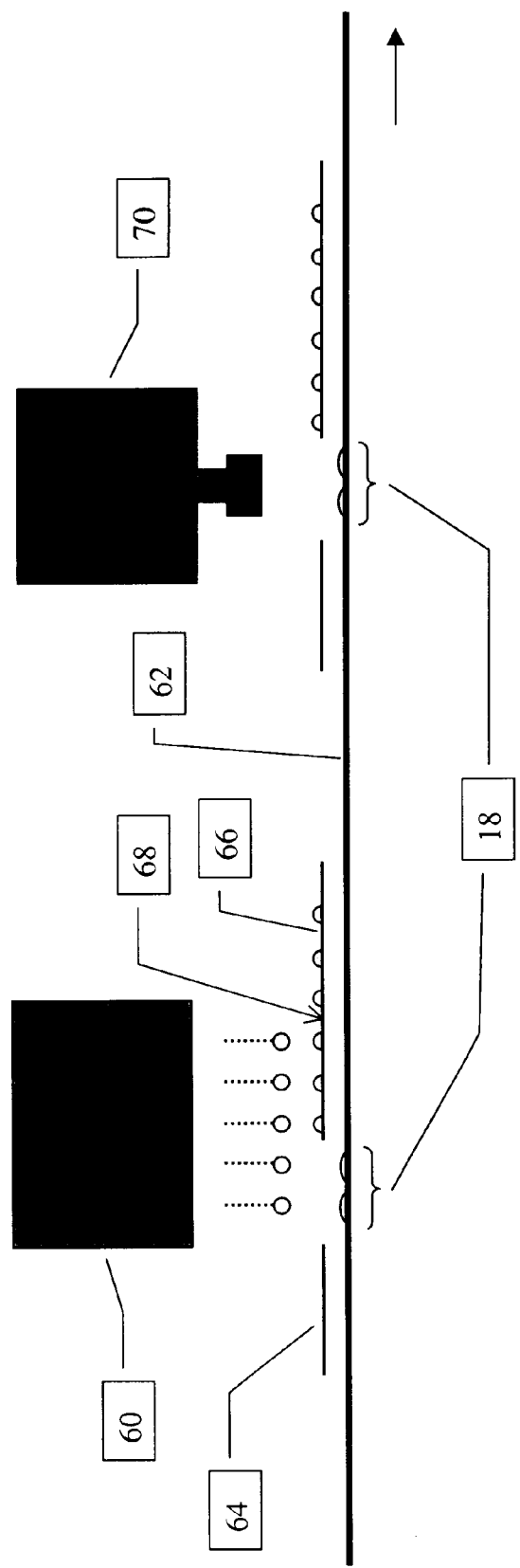
FIG. 8 is a schematic of a nonimpact printing process of this invention.

FIG. 8 depicts a schematic of an apparatus for nonimpact printing of reagent onto the reagent area of a substrate of the present invention. Print head 60 repeatedly ejects a stream of reagent droplets onto web 62, which moves in the direction shown by the arrow. Optional masks 64 and 66 ensure that the droplet stream only reaches web 62 in reagent areas 18.

To control the printing, mask 66; i.e., the mask closest to print head 60, optionally has a hydrophobic surface 68 facing the print head. Reagent from the multiple dispenser nozzles of print head 60 forms multiple reagent dots on mask surface 68. Because the surface is hydrophobic, the dots remain isolated and can be individually viewed by a downstream optical system 70. The hydrophilicity of surface 18 causes the droplets arriving on that surface to spread and/or coalesce, so it is more difficult for optical system 70 to detect individual dots directly on the reagent area.

Optical system 70 can detect and, if desired, reject defective product. For example, an absence of dots may indicate that one or more dispenser nozzles are defective. Among the suitable optical detection methods are dark field microscopy, shadowing, patterning, laser illumination, etc. Optionally, a colorant, or a fluorescent dye, can be added to the reagent to make it more easily visible to optical system 70. For example, methylene blue dye, added to a reagent to about 0.1% final concentration, makes the reagent visible to an optical system, without substantially altering the measurements made with the reagent.

Print head 60 may be any nonimpact print head known in the art, including ultrasonic, electrographic, ion projection, etc. Preferably, print head 60 is an ink-jet print head, more preferably, a thermal ink-jet print head.

The following examples demonstrate the present invention in its various embodiments, but are not intended to be in any way limiting.

EXAMPLE 1 (COMPARATIVE EXAMPLE)

Figure 9:
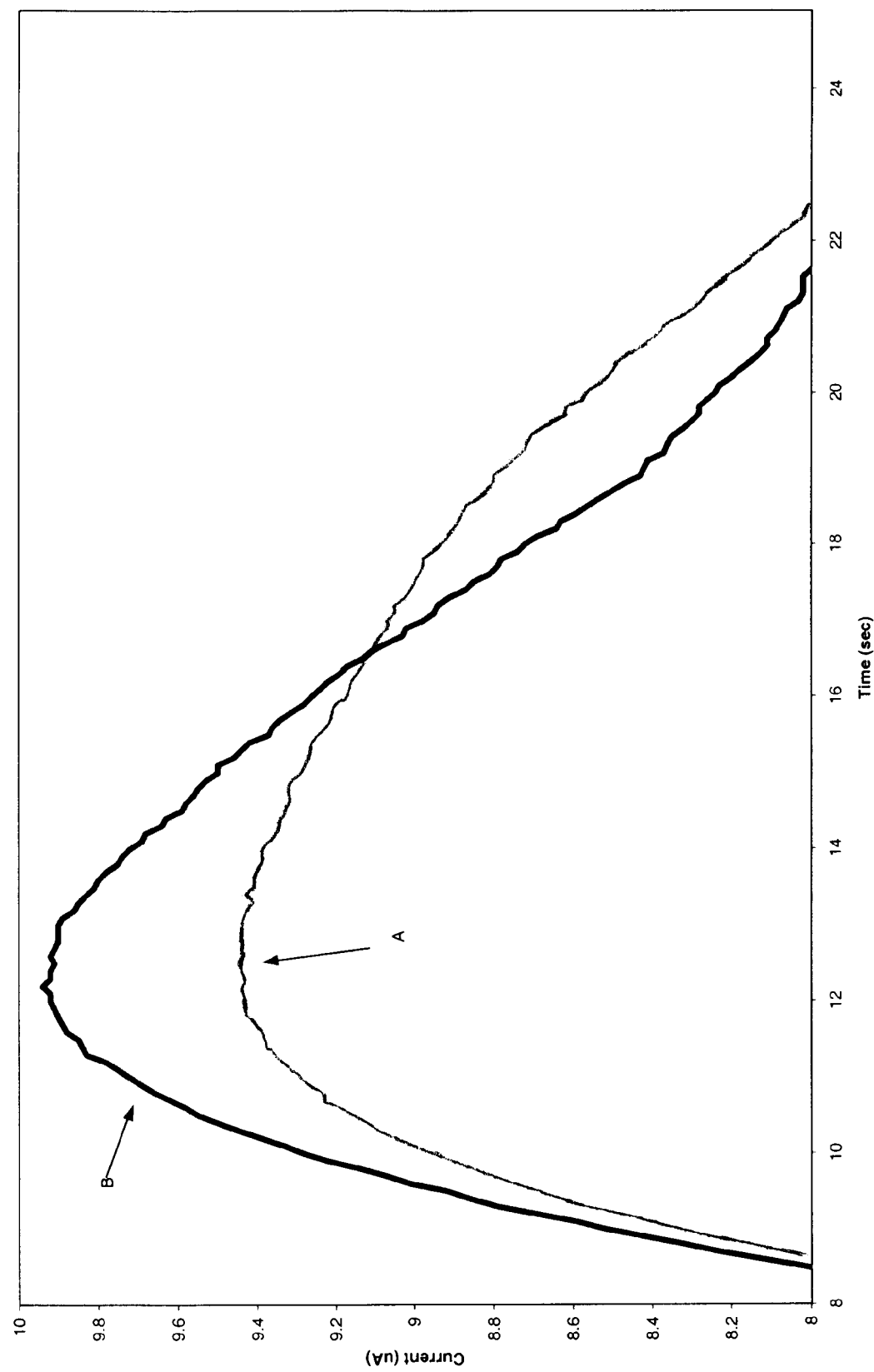
FIG. 9 is a graph that demonstrates an advantage of the present invention.

Two strips of the type described above for PT measurements were prepared (see FIGS. 1–3). The difference between the strips was that strip A had a bottom layer 28 of untreated polyethylene terephthalate, while strip B had a bottom layer 28 of FMC GelBond Film. A blood sample was applied to each strip and PT measurements made in an apparatus of the type depicted in FIG. 4. FIG. 9 depicts the resultant clotting curves. The curve for strip A has a relatively flat peak (corresponding to peak 3 in FIG. 5). The flatness of the peak limits the precision of the resultant PT calculation. By contrast, the curve for strip B has a much sharper peak, which permits much greater precision. (Note that the PT times for the samples measured with the two strips are different.)

EXAMPLE 2

A device of this invention is made by first passing a double-sided adhesive tape (RX 675SLT, available from Scapa Tapes, Windsor, Conn.) sandwiched between two release liners into a laminating and rotary die-cutting converting system. The pattern shown in FIG. 2, with the exception of the stop junction, is cut through the top release liner and tape, but not through the bottom release liner, which is then removed as waste, along with the cutouts from the tape. 3M Antifog Film is laminated to the exposed bottom side of the tape. Reagent (thromboplastin, available from Ortho Clinical Diagnostics, Raritan, N.J.) is then printed onto the reagent area (18) of the film by thermal ink-jet printing, using printing heads 51612A, from Hewlett Packard, Corvallis, Oreg. A sample port is cut in untreated polyester film (AR1235, available from Adhesives Research, Glen Rock, Pa.) and then laminated, in register, to the top of the double-sided tape (after removing the release layer). A die then cuts the stop junction through the three layers of the sandwich. Finally, strips of single-sided adhesive tape—Catalog No. 9843 (MSX4841), available from 3M, St. Paul, Minn.—are applied to the outside of the polyester layers to seal the stop junction.

EXAMPLE 3

A procedure that is similar to the one described in Example 1 is followed to make a strip of the type depicted in FIG. 6. Reagent that is thermal ink-jet printed onto areas 118P, 218P, and 318P is, respectively, thromboplastin; thromboplastin, bovine eluate, and recombinant Factor VIIa; and thromboplastin and bovine eluate alone. The bovine eluate (plasma barium citrate bovine eluate) is available from Haemotologic Technologies, Burlington, Vt.; and recombinant Factor VIIa from American Diagnostica, Greenwich, Conn.

Measurements made on a whole blood sample using the strip of this Example yield a curve of the type shown in FIG. 5 for each of the reagent areas. The data from the curves for the controls (reagent areas 218P and 318P) are used to qualify the data from the curve for reagent area 118P. As a result, the PT time can be determined more reliably than can be done with a strip having a single reagent area.

We claim:

1. A diagnostic reagent device for measuring an analyte concentration or characteristic of a biological fluid, including a non-absorbent substrate comprising:
    a) a sample application area for accepting a sample of the biological fluid for analysis; and
    b) a predetermined hydrophilic surface area for receiving, by nonimpact printing, a pulsed stream of microdroplets of a diagnostic reagent liquid comprising thromboplastin that interacts with the sample to cause in the sample a physically-measurable change that can be related to the analyte concentration or characteristic of the fluid.

2. The device of claim 1, in which the sample application area is located on said at least one hydrophilic surface area.

3. The device of claim 1, in which the substrate comprises a substantially transparent planar sheet.

4. The device of claim 1, in which the substrate comprises a substantially transparent thermoplastic sheet.

5. The device of claim 1, in which the reagent liquid comprises a colorant.

6. The device of claim 1, in which the predetermined hydrophilic surface area has a water contact angle of no more than about 60°.

7. The device of claim 6, in which said water contact angle is about 25°.

8. The device of claim 1, further comprising means for conveying the sample from the application area to the reagent area.

9. The device of claim 8, in which the means for conveying the sample from the application area to the reagent area comprises a top layer, separated from the substrate by an intermediate layer that has a through hole and adjoining channel cut into it, wherein the top layer, intermediate layer, and substrate form a bladder that, when compressed, and released causes a reduced pressure in the channel that draws blood into the reagent area.

10. The device of claim 9, in which the top layer has a hydrophobic surface facing the substrate, at least in the channel and reagent area.

11. A method for preparing a medical diagnostic reagent device, comprising the steps of
    (a) providing a non-absorbent substrate having at least one hydrophilic target surface area,
    (b) providing from a nonimpact print head onto a point within the hydrophilic surface area a pulsed stream of microdroplets of a diagnostic reagent liquid, in which the reagent liquid comprises thromboplastin,
    (c) moving the substrate relative to the steam, and
    (d) repeating steps b) and c) at least enough times to provide a substantially uniform layer of the liquid over the hydrophilic surface area.

* * * * *